US010772734B2

(12) United States Patent
Boublil et al.

(10) Patent No.: US 10,772,734 B2
(45) Date of Patent: Sep. 15, 2020

(54) ARTHRODESIS IMPLANT AND INSTRUMENT FOR GRIPPING SUCH AN IMPLANT

(71) Applicant: IN2BONES, Ecully (FR)

(72) Inventors: Daniel Edmond Boublil, Lyons (FR); Jean-Yves Paul Albert Coillard-LAvirotte, Saint Cyr au Mont d'Or (FR)

(73) Assignee: IN2BONES, Ecully (FR)

( * ) Notice: Subject to any disclaimer, the term of this patent is extended or adjusted under 35 U.S.C. 154(b) by 175 days.

(21) Appl. No.: 15/504,488

(22) PCT Filed: Aug. 7, 2015

(86) PCT No.: PCT/FR2015/052179
§ 371 (c)(1),
(2) Date: Jul. 18, 2017

(87) PCT Pub. No.: WO2016/027025
PCT Pub. Date: Feb. 25, 2016

(65) Prior Publication Data
US 2017/0239059 A1    Aug. 24, 2017

(30) Foreign Application Priority Data

Aug. 18, 2014    (FR) ..................... 14 57860

(51) Int. Cl.
*A61F 2/42*     (2006.01)
*A61F 2/30*     (2006.01)
*A61F 2/46*     (2006.01)

(52) U.S. Cl.
CPC ........ *A61F 2/4241* (2013.01); *A61F 2/30771* (2013.01); *A61F 2/4225* (2013.01);
(Continued)

(58) Field of Classification Search
CPC combination set(s) only.
See application file for complete search history.

(56) References Cited

U.S. PATENT DOCUMENTS

| 5,601,558 A *    | 2/1997 | Torrie ............... A61B 17/0401 |
|                  |        |                               411/495 |
| 2008/0132894 A1* | 6/2008 | Coilard-Lavirotte ...................... |
|                  |        |                               A61B 17/1604 |
|                  |        |                               606/60 |

(Continued)

FOREIGN PATENT DOCUMENTS

| EP | 0 611 557 A2 | 8/1994 |
| FR | 2 935 601 A1 | 3/2010 |
| WO | WO 2011/110784 A1 | 9/2011 |

OTHER PUBLICATIONS

International Search Report in connection with PCT International Application No. PCT/FR2015/052179.

*Primary Examiner* — David H Willse
*Assistant Examiner* — Javier G Blanco
(74) *Attorney, Agent, or Firm* — John P. White; Paul Teng; Cooper & Dunham LLP

(57) ABSTRACT

An arthrodesis implant (1) allowing promoting the bone fusion of two bones is provided, the implant (1) comprising: a rigid and non-deformable anchoring body (4), designed to ensure the anchoring of the implant (1) in a first bone (2), and a deformable portion (5) designed to ensure the anchoring of the implant (1) in a second bone. The deformable portion (5) comprises at least two anchoring arms (9, 10) which protrude beyond the anchoring body (4) from the base end (7) of the anchoring body (4), the anchoring arms (9, 10) being separated from each other by a free space (E) so as to be able to be brought closer to each other by deformation of the anchoring arms under the action of the second bone. At least one of the anchoring arms (9, 10) is provided with a (Continued)

longitudinal reinforcing fin protruding beyond the anchoring arm (9, 10) from a lateral side (20) of the anchoring arm (9, 10).

17 Claims, 2 Drawing Sheets

(52) U.S. Cl.
CPC .... *A61F 2/4606* (2013.01); *A61F 2002/3028* (2013.01); *A61F 2002/30158* (2013.01); *A61F 2002/30179* (2013.01); *A61F 2002/30205* (2013.01); *A61F 2002/30224* (2013.01); *A61F 2002/30622* (2013.01); *A61F 2002/30892* (2013.01); *A61F 2002/30904* (2013.01); *A61F 2002/4228* (2013.01); *A61F 2002/4243* (2013.01)

(56) References Cited

U.S. PATENT DOCUMENTS

| | | |
|---|---|---|
| 2009/0210016 A1 | 8/2009 | Champagne |
| 2011/0144644 A1* | 6/2011 | Prandi .................... A61B 17/68 606/62 |
| 2011/0184528 A1* | 7/2011 | Beckendorf .......... A61F 2/4225 623/23.42 |
| 2013/0066435 A1* | 3/2013 | Averous ............. A61B 17/7266 623/21.11 |
| 2013/0131822 A1* | 5/2013 | Lewis ................... A61F 2/4606 623/21.19 |

\* cited by examiner

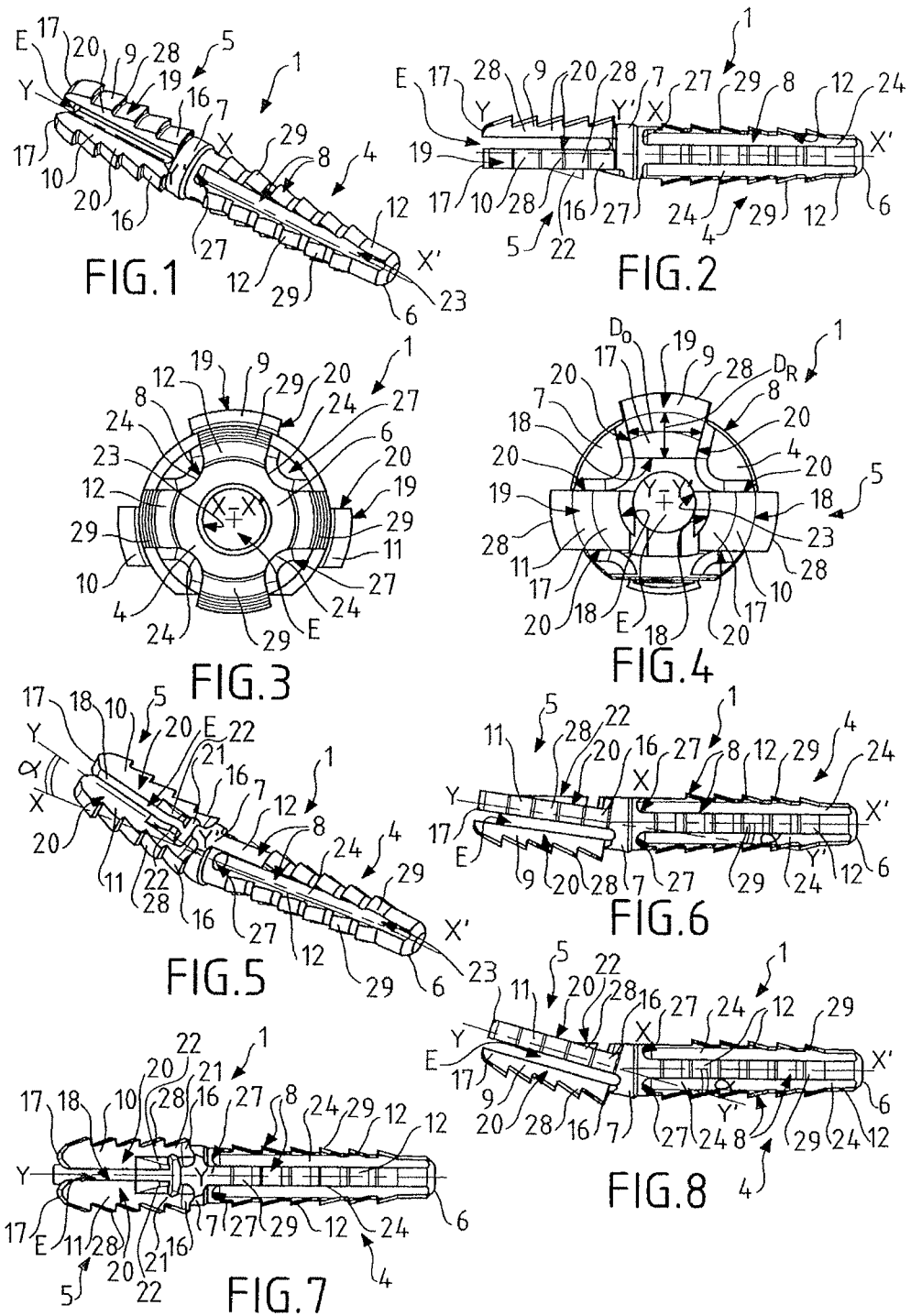

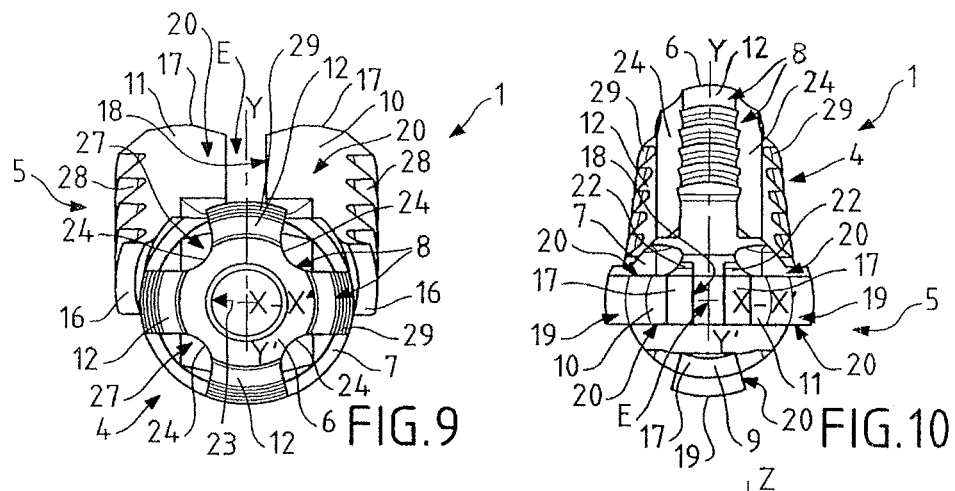
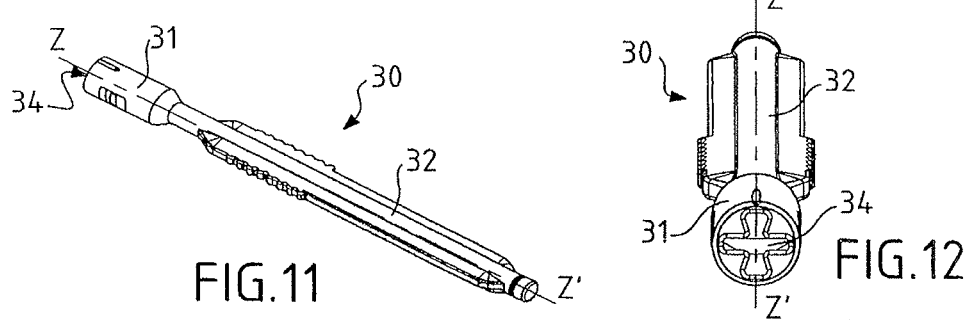
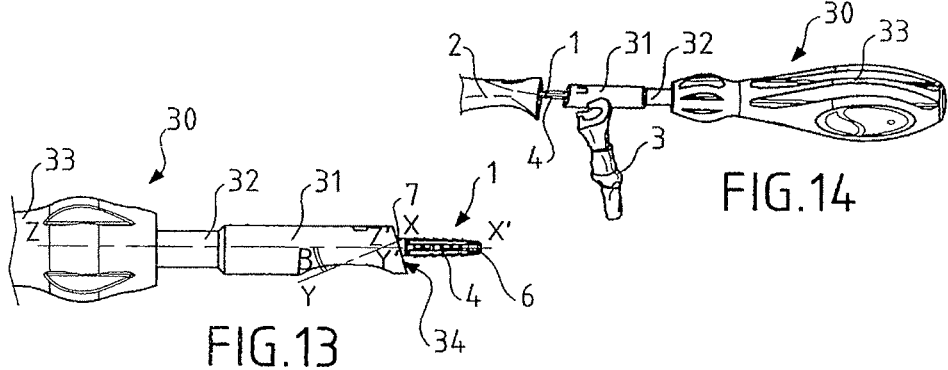
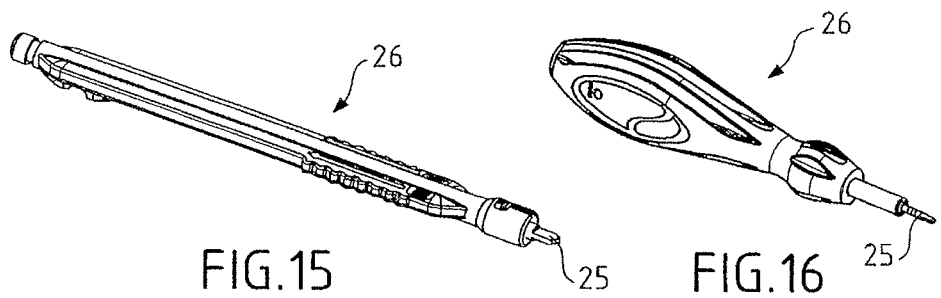

ARTHRODESIS IMPLANT AND INSTRUMENT FOR GRIPPING SUCH AN IMPLANT

CROSS-REFERENCE TO RELATED APPLICATIONS

This application is a § 371 national stage of PCT International Application No. PCT/FR2015/052179, filed Aug. 7, 2015, claiming priority of French Patent Application No. FR 1457860, filed Aug. 18, 2014, the content of each of which is hereby incorporated by reference into the application.

TECHNICAL FIELD

The invention relates to the general field of osteosynthesis surgical implants, and in particular to phalangeal implants intended to be placed in the body of a patient, at the hand or the foot of the latter, in order to allow the fusion of two phalanges.

More specifically, the invention concerns an arthrodesis implant allowing promoting the bone fusion of a first bone with a second bone, said implant comprising:
- a substantially rigid and non-deformable anchoring body, designed to ensure the anchoring of the implant in the first bone, the anchoring body extending between an end for penetration in said first bone and an opposite base end, and
- a deformable portion designed to ensure the anchoring of the implant in the second bone, said deformable portion comprising at least two anchoring arms which protrude beyond the anchoring body from the base end of the latter, the anchoring arms being separated from each other by a free space so as to be able to be brought closer to each other by deformation of said anchoring arms under the action of the second bone.

The invention also concerns an instrument for gripping an arthrodesis implant.

PRIOR ART

In order to treat certain bone pathologies, and in particular of phalanges, such as inter-phalangeal deformations, claw or hammer toes, or else arthrosis, performing an arthrodesis is sometimes necessary, that is to say causing an interbone fusion in order to fasten one bone relative to the other.

In the case of phalanges, for example, it is known to place an intramedullary implant during a surgical operation, which aims to secure two phalanges relative to one another, in order to cause their bone fusion. In this case, this type of surgical implant includes a distal portion intended to be anchored in the medullary canal of one of the two phalanges, and a proximal portion which may be anchored in the medullary canal of the second phalange.

Such known arthrodesis implants are most often made so as to form an integral single part, which allows improving their longevity in the body of the patient, so as, for example, not to require to be removed from said body. Furthermore, such a design may sometimes allow reducing the manufacturing cost.

Nevertheless, the use of a single material might, in some cases, not entirely fit to the anatomy of the patient. Indeed, in most patients, within the same skeleton, certain bone bodies frequently has different hardnesses, such that the hardness or the flexibility of a given implant may, while being particularly adapted to the hardness of one of the two phalanges, not be adapted to the hardness of the other phalange. More generally, the implant may be inadequate for its placement environment, due to the high variability of the latter.

A too significant inadequacy of the hardness of the material to the bone is likely to be a source of pain, to the extent that the implant, when it is too rigid or too hard in comparison with the mechanical properties of the bone, may damage said bone during the placement, or a posteriori, in particular in the case of a patient having a weakened bone structure. This inadequacy may also be the cause of an increase in the duration of the therapy, to the extent that the osteosynthesis, that is to say the bone reconstruction, may be disturbed by the too high hardness of the implant towards one of the bones.

On the contrary, a too significant flexibility may cause an accidental dislocation of the implant from the medullary canal, or else infections, in particular in an elderly patient. Moreover, a bone with a too significant rigidity in comparison with the implant, is likely to wear the latter, so as to prejudicially affect its longevity. Such an implant thus has the risk, in case of a too significant wear, of requiring removal from the patient's body during a second surgical operation for removing said implant. Of course, this involves a substantial additional cost, a waste of time, and a potential risk to the patient's health, in particular in the case of an elderly patient.

Moreover, the placement of known implants may sometimes turn out to be difficult, in particular in the case where the implant is particularly flexible. Indeed, though the surgeon may use a gripping tool to firmly hold the implant when it is introduced into the medullary canal of the bone, the flexible portion of the implant that is introduced may be inappropriately deformed upon insertion, and make this operation difficult and inaccurate.

Thus, the known implants do not appear to have sufficient features to be, at the same time, easy to put in place, reliable, robust, and versatile so as to adapt to the morphology of each patient while allowing a relatively rapid and painless arthrodesis.

DISCLOSURE OF THE INVENTION

The objects assigned to the present invention consequently aim to remedy to the different drawbacks enumerated hereinbefore and to propose a new implant and a new instrument for gripping such an implant, particularly adapted to the physiology and to the morphology of the patient, and having a high versatility of use and adaptation to its placement environment.

Another object of the invention aims to propose a new implant and a new instrument for gripping such an implant, whose holding in the body of the patient is particularly reliable.

Another object of the invention aims to propose a new implant and a new instrument for gripping such an implant, particularly robust and resistant.

Another object of the invention aims to propose a new implant and a new instrument for gripping such an implant, allowing limiting the pain suffered by the patient.

Another object of the invention aims to propose a new implant and a new instrument for gripping such an implant, allowing treating a bone pathology of the patient in a particularly effective and rapid manner.

Another object of the invention aims to propose a new implant and a new instrument for gripping such an implant, easy to put into place in the body of the patient.

Another object of the invention aims to propose a new implant and a new instrument for gripping such an implant, whose manufacture is relatively easy.

Another object of the invention aims to propose a new implant and a new instrument for gripping such an implant, allowing reducing the cost of the surgical operation for placing the implant.

Another object of the invention aims to propose a new implant and a new instrument for gripping such an implant, allowing reducing any risk to the patient's health related to the implant placement and the therapy.

The objects assigned to the invention are achieved by means of an arthrodesis implant allowing promoting the bone fusion of a first bone with a second bone, said implant comprising:
- a substantially rigid and non-deformable anchoring body, designed to ensure the anchoring of the implant in the first bone, the anchoring body extending between an end for penetration in said first bone and an opposite base end, and
- a deformable portion designed to ensure the anchoring of the implant in the second bone, said deformable portion comprising at least two anchoring arms which protrude beyond the anchoring body from the base end of the latter, the anchoring arms being separated from one another by a free space so as to be able to be brought closer to each other by deformation of said anchoring arms under the action of the second bone.

and being characterized in that at least one of the anchoring arms is provided with a longitudinal reinforcing fin protruding beyond the anchoring arm from a lateral side of the latter.

The objects assigned to the invention are also achieved by means of an instrument for gripping an implant according to the invention, the gripping instrument comprising a removable bit for securing the implant with the gripping instrument, via the deformable portion of said implant.

BRIEF DESCRIPTION OF THE DRAWINGS

Other features and advantages of the invention will appear and come out in more details upon reading the description made hereinafter, with reference to the appended drawings, given only as an illustrative and non-limiting example, in which:

FIG. 1 illustrates, in a general perspective view, a first variant of an implant in accordance with the invention, which comprises coaxial anchoring body and deformable portion;

FIG. 2 represents the implant of FIG. 1 in a side view;

FIGS. 3 and 4 each illustrate the implant of FIG. 1 respectively in an axial view facing the anchoring body, and in an axial view facing the deformable portion;

FIG. 5 illustrates a second variant of an implant in accordance with the invention in a general perspective view, in which the anchoring body and the deformable portion are inclined relative to one another by approximately 10 degrees;

FIGS. 6 and 7 illustrate the implant of FIG. 5 according to side views;

FIG. 8 represents, in a side view, a third variant of an implant in accordance with the invention for which the anchoring body and the deformable portion are inclined relative to one another by about 17 degrees;

FIGS. 9 and 10 each illustrate the implant of FIG. 8 respectively in an axial view facing the anchoring body, and in an axial view facing the deformable portion;

FIGS. 11 and 12 represent, according to perspective views, a gripping instrument in accordance with the invention, allowing grasping the implant of FIGS. 1 to 10;

FIGS. 13 and 14 schematically represent, in side views, the gripping instrument of FIGS. 11 and 12 associated with the implant of FIGS. 5 to 10;

Finally, FIGS. 15 and 16 illustrate instruments for opening a medullary canal of a bone prior to anchoring the implant of FIGS. 1 to 10 in said bone.

BEST MODE FOR CARRYING OUT THE INVENTION

The invention concerns, as such, an arthrodesis implant 1 (as illustrated, for example, in FIGS. 1 to 10), that is to say a surgical implant 1 intended to be placed in the body of a patient, human or animal, at his/its bones, for example during a surgical operation performed under local or general anesthesia. The implant 1 of the invention allows performing an arthrodesis of a first bone 2 with a second bone 3, that is to say that it allows promoting the bone fusion of said first bone 2 with said second bone 3. At the end of a successful arthrodesis and performed using the implant 1, the first bone 2 and the second bone 3 are advantageously secured to each other in an integral manner. Bone fusion is preferably performed at an articulation connecting the first bone 2 to the second bone 3, so as to replace said articulation.

Such a surgical operation may, for example, allow, in the case where the patient suffers, for example, from interarticular arthrosis, removing the pain suffered by the patient by fusing the affected articulation. Alternatively, the operation allows treating, for example, an inter-phalangeal deformation, or claw or hammer toes.

Thus, the implant 1 of the invention may advantageously be inserted at the articulation between two bones, for example an articulation between two bones of the spinal column, the knee or of the elbow. Preferably, the implant 1 of the invention is a phalangeal implant 1, the first bone 2 forming a first phalange and the second bone 3 forming a second phalange of the same finger as the first phalange, as illustrated as example in FIGS. 13 and 14. The concerned phalanges are, for example, located in a foot of the patient or in a hand of the latter. Once the arthrodesis has been performed, the articulation between the two concerned phalanges of the same finger or toe is advantageously blocked, such that said finger or toe is no longer capable of being folded at this articulation in particular.

The implant 1 is advantageously provided to be left in the body of the patient at the end of the operation, throughout the life of said patient, and to not require an ablation of said implant 1 once the arthrodesis has been performed. Of course, the implant 1 may be designed on the contrary so as to be able to be removed from the body of the patient at the end of the arthrodesis.

As illustrated in FIGS. 1 to 10, the implant 1 of the invention comprises an anchoring body 4 designed to anchor the implant 1 in the first bone 2, and a deformable portion 5 designed to ensure the anchoring of the implant 1 in the second bone 3. The anchoring body 4 and the deformable portion 5 are secured to one another and preferably disposed in opposition to one another, for example on either side of an intermediate or median plane. The implant 1 of the invention may thus be anchored on the one hand in the first bone 2 via the anchoring body 4, and on the other hand in the second bone 3 via the deformable portion 5, such that the first bone 3 and the second bone 4 are connected to each other by the implant 1. The anchoring body 4, and respectively the deformable portion 5, is advantageously designed to be planted in the concerned bone, or inserted forcibly, in the same manner as a fastening peg. Once the implant 1 is anchored in the first bone 2 and in the second bone 3, the latter become secured to each other via the implant 1, in a flexible or rigid manner, such that an osteosynthesis takes place leading to the bone fusion of said first and second bones 3. Preferably, the anchoring of the anchoring body 4 is effected by impaction, or by a forced wedging, of the latter in the first bone 2, in the same manner as a peg. The anchoring body 4 is advantageously designed to be thus anchored, and is for example devoid of means for screwing said anchoring body 4 into the first bone 2. Likewise, the anchoring of the deformable portion 5, is preferably performed by impaction, or by forced wedging, of the latter in the second bone 3. The deformable portion 5 is thus advantageously devoid of means for screwing the latter into the second bone 3.

Preferably, the anchoring body 4, as well as the deformable portion 5, are intended to be inserted into the medullary canal respectively of the first bone 2 and of the second bone 3, such that the implant 1 of the invention preferably forms an intramedullary implant 1. In this case, the anchoring body 4 is preferably intended to be anchored in the medullary canal of the first bone 2, the deformable portion 5 being intended to be anchored in the medullary canal of the second bone 3. The anchoring body 4 and the deformable portion 5 may in this case be implanted in the medullary canals of the first and second bones 3, for example after the end of the concerned bone (formed for example by an external cartilaginous surface) has been pierced or removed from said bone in order to form an access opening to said medullary canal. The internal bone stock of the medullary canal of the first bone 2, respectively of the second bone 3, should also preferably be arranged to allow the reception of the anchoring body 4. FIGS. 13 and 14 represent, in this regard, examples of instruments 26 for opening a medullary canal of a bone prior to anchoring the implant 1 of the invention in the first and second bones 3. These opening instruments 26 are preferably provided with a bit 25 for piercing the bone. Other instruments or tools may of course be used.

Of course, without departing from the scope of the invention, the anchoring body 4 and/or the deformable portion 5 may be designed to be anchored in any other part of the bone, and for example to be anchored in an orifice formed in the cortical part of the bone.

In the preferred case where the implant 1 is intra-medullary, the anchoring body 4, and the deformable portion 5 respectively are advantageously shaped to be axially inserted into the medullary canal of the first bone 2, respectively of the second bone 3. The anchoring body 4 is thus preferably designed to be anchored in the first bone 2 coaxially with the latter, and the deformable portion 5 in the second bone 3 coaxially with the latter. In particular, the medullary canal of such bones having a substantially cylindrical generally tubular shape, the anchoring body 4 and the deformable portion 5 will preferably have a generally elongate and axial, and preferably cylindrical, conical, prismatic or cruciform shape, as illustrated in FIGS. 1 to 10, and will be shaped to be inserted coaxially with the tubular shape of the concerned medullary canal, so as to be able to be wedged within the medullary canal. In particular, in the preferred case where the first bone 2 and the second bone 3 are phalanges, the medullary canal advantageously has a shrinkage, forming, for example, the isthmus of the phalange, which allows applying a centripetal pressure for wedging the implant 1 within the medullary canal, and in particular of the anchoring body 4 and/or the deformable portion 5, this centripetal pressure allows retaining by adherence the implant 1 within the medullary canal. The implant 1, its anchoring body 4 and its deformable portion 5, will preferably be chosen, shaped and sized so as to adapt to the morphology of the bones in which they are anchored, and possibly based on the morphology of the patient.

As illustrated in FIGS. 1 to 10, the anchoring body 4 of the invention extends between an end 6 for penetration in said first bone 2 and an opposite base end 7, and thus has an elongated shape, preferably along an axis X-X'. The penetrating end 6 forms a free end of the implant 1, and is advantageously tapered, conical, curved or chamfered to facilitate its penetration into the first bone 2. The opposite base end 7 forms an attachment point of the anchoring body 4 with the rest of the implant 1, and in particular with the deformable portion 5. Preferably, the anchoring body 4 has an outer surface 8 connecting the base end 7 to the penetrating end 6, and forms, for example, a solid body delimited by said outer surface 8. Alternatively, as described hereinafter, the anchoring body 4 may be cannulated. Preferably, the outer surface 8 has a generally convergent shape, for example conical, in the direction of the penetrating end 6, for example along the axis X-X', which allows improving the wedging of the anchoring body 4 in the first bone 2, the anchoring body 4 thus being able, for example, to adapt to several diameters of medullary canals. The anchoring body 4 thus preferably has a section with a greater size for example in length, width or diameter in the proximity of the base end 7 than in the proximity of the penetrating end 6. Alternatively, the anchoring body 4 may have a generally prismatic shape along the axis X-X', and not be convergent, without thereby departing from the scope of the invention. In the context of the invention, by <<general shape>> is meant the external shape of the concerned member, that is to say not including in particular the various asperities, grooves, chamfers, fins, throats, teeth, and other protruding or recessed members.

The anchoring body 4 of the invention is substantially rigid and non-deformable, or at least the anchoring body 4 is less easily deformable than the deformable portion 5, and requires a greater force to be deformed. Thus, the anchoring body 4 is advantageously designed to be anchored in the first bone 2, in particular in the case where the latter forms a bone which is more resistant or of greater hardness than the second bone 3. According to such a design, the implant 1 is particularly adapted to the morphology of the skeletal framework of the patients, in the case where the bones to be fused are of different resistance, for example in the case where the first bone 2 forms a proximal phalange, and the second bone 3 a distal phalange, that is to say external, of the patient's finger or toe. The deformable portion 5 being designed anchored in the second bone 3 and being more deformable than the anchoring body 4, its anchoring is not such as to deteriorate the second bone 3, and allows a good bone reconstruction following the insertion of the implant 1. The holding in the first bone 2 of the anchoring body 4 is particularly both reliable and solid, and the implant 1 is particularly resistant.

In particular, the structure and/or the material forming the anchoring body 4 are advantageously chosen and designed so that the anchoring body 4 does not deform, or minimally, under the action of the first bone 2, when the anchoring body 4 is anchored in said first bone 2. In particular, the anchoring body 4 is designed so as not to bend along the longitudinal axis X-X', or not to contract under the effect of an axial or radial pressure, when it is introduced, and possibly anchored, in the first bone 2. Nevertheless, locally, the anchoring body 4 may undergo deformations such as to allow holding its anchoring in the first bone 2; In particular, the anchoring body 4 may comprise retention members (described hereinafter) which may be deformed by the second bone 3, in particular at the isthmus of the medullary canal, in order to allow a good retention of the anchoring body 4 within said second bone 3.

Preferably, the structure and the shape of the anchoring body 4 confer it, or at least contribute to confer it, its rigid character. For this purpose, the anchoring body 4 preferably forms a solid and massive body (as illustrated in FIGS. 5 to 10), or a tubular body (as illustrated in FIGS. 1 to 4). The anchoring body 4 preferably comprises longitudinal reinforcing ribs 12, which are, for example, distributed around the axis X-X', protruding from the outer surface 8 in the direction of the length of the anchoring body 4, for example from the penetrating end 6. The longitudinal reinforcing ribs 12, advantageously allow stiffening the anchoring body 4, in particular in flexion and in torsion, without the latter having a too significant thickness.

According to the invention, the deformable portion 5 comprises at least two anchoring arms 9, 10, 11 which protrude beyond the anchoring body 4 from the base end 7 of the latter. As illustrated in FIGS. 1 to 10, the anchoring arms 9 of the invention rise beyond the anchoring body 4, from the base end 7, and all of them are orientated in a similar direction along an axis Y-Y', which is preferably opposite to the direction of the anchoring body 4. The axis Y-Y' thus forms the general direction of extension of the deformable portion 5, the latter being the result of the combination of the anchoring arms 9, 10, 11, which advantageously form a beam of anchoring arms 9, 10, 11. Each anchoring arm 9, 10, 11 advantageously extends between one junction end 16 with the anchoring body 4 and an opposite terminal end 17 for implanting said anchoring arm 9 in the second bone 3, along a proper axis of extension.

Preferably, the anchoring arms 9, 10, 11 have a section orthogonal to their proper axis of extension which is less significant than the section orthogonal to the axis X-X' of the anchoring body 4. The anchoring arms 9, 10, 11 are thus preferably thinner than the anchoring body 4, which confers them a more significant deformability than that of the latter. The anchoring arms 9, 10, 11 are therefore preferably flexible, in an elastic or elastoplastic manner, so that the deformable portion 5 which they form is generally easier to deform than the anchoring body 4. The deformable portion 5 may thus advantageously be anchored in the second bone 3, in particular when the latter is softer, more fragile and/or thinner than the first bone 2. In addition, the deformable portion 5 adapts, by deformation, to the shape of the second bone 3, and in particular its medullary canal, in order to be able to be anchored reliably, safely and painlessly for the patient. The implant 1 is thus particularly adapted to the mechanical and morphological characteristics, of both the first bone 2 and the second bone 3, such that its connection with the latter is particularly reliable, the pain suffered by the patient relatively low, and the duration of the treatment reduced. The deformability and flexibility of the anchoring arms 9,10,11 further confers the connection between the first bone 2 and the second bone 3 formed by the implant 1 a certain flexibility which is such as to stimulate the natural osteosynthesis, and accelerate the bone fusion.

The preferred variant of the invention represented in FIGS. 1 to 4 forms a straight implant 1, that is to say in which, preferably, the anchoring body 4 extends along an axis X-X', the deformable portion 5 extending in an opposite direction of the anchoring body 4 along an axis Y-Y' coaxial with the axis X-X'. Such an implant 1 is particularly adapted in the case where the first bone 2 and the second bone 3 should be disposed coaxially, preferably so that their medullary canals are coaxial.

Another preferred variant of the invention represented in FIGS. 5 to 10 forms a bent implant 1, that is to say in which, preferably, the anchoring body 4 extends along an axis X-X' and the deformable portion 5 extending in a direction opposite to the anchoring body 4 along an axis Y-Y' secant to the axis X-X', such that the axis Y-Y' is inclined relative to the axis X-X' at an elevation angle α comprised between:
- 8 and 12 degrees, preferably about 10 degrees (as illustrated in FIGS. 5 to 7), or
- 15 and 19 degrees, preferably about 17 degrees (as illustrated in FIGS. 8 to 10).

Such an implant 1 is particularly adapted in the case where the first bone 2 and the second bone 3 should be disposed in a secant manner, for example slightly secant, at this same elevation angle α, preferably so that their medullary canals are secant at this same elevation angle α. Of course, the implant 1 might be designed with a different elevation angle α depending on the bone morphology and the desired orientation between the first bone 2 and the second bone 3. Preferably, the value of the angle α corresponds to an anatomical value of the natural orientation of the first bone 2 relative to the second bone 3.

Preferably, the implant 1 forms a one-piece single part, the deformable portion 5 being made integral with the anchoring body 4. In particular, the anchoring arms 9, 10, 11 preferably extend the anchoring body 4 and are integral with the latter so that the implant 1 is formed of one single piece, which confers a high structural resistance to the implant 1, and facilitates its manufacture, which may be performed for example by molding and machining, without any step of assembling parts attached to each another. The implant 1 may advantageously be made using a single material, the deformability of the different members which constitute it being obtained by acting on the shape of the latter, and in particular by acting on their section and/or their thickness. The implant 1 is preferably made of a polymeric material, for example PEEK, which allows, for example, being both radio-transparent, biocompatible, light and inexpensive to manufacture. Of course, without departing from the scope of the invention, the implant 1 may be made of another material, for example a metal material of the stainless or titanium type. Also, the implant 1 may be the result of the assembly of several parts, and not be a one-piece part.

According to the invention, the anchoring arms 9, 10, 11 are separated from one another by a free space E so as to be able to be brought closer to one another by deformation of said anchoring arms 9, 10, 11 under the action of the second bone 3. Thus, the anchoring arms 9, 10, 11 of the invention substantially do not touch each other, at least when they are not deformed, a space being advantageously formed between each of them, over at least a portion of their length, or still over their entire length. The anchoring arms 9, 10, 11 thus have a free central space therebetween, so that it may be deformed so as to fill in this free space E. Such a design preferably makes the deformable portion 5 compressible in a centripetal manner relative to the axis Y-Y', and/or capable of being twisted about said axis Y-Y', and/or capable of being bent, the anchoring arms 9 being preferably free to occupy, at least in part, the free space E which separates them, under the action of the second bone 3 when they are anchored in the latter. The elasticity of the anchoring arms 9, 10, 11 preferably allows the deformable portion 5 to apply a centrifugal pressure to the medullary canal (or generally to the anchoring housing), which is such as to help retaining the implant 1 within the second bone 3, for example by adherence. Preferably, the anchoring arms 9, 10, 11 are designed to evolve between a non-deformed configuration, which constitutes their initial position, and in which the free space E is effectively free, and a deformed position in which they are brought close to one another, or even touch, and fill in the initial free space E. Preferably, the anchoring arms 9, 10, 11 are elastically deformable, so as to return by themselves substantially to their non-deformed configuration when they are spaced apart therefrom.

The deformable portion 5 thus forms a reliable, flexible and versatile connection, such that the implant 1 may be anchored to both a first bone 2 and a second bone 3 which are of different nature, resistance and shape.

Preferably, the deformable portion 5 is formed by three anchoring arms 9, 10, 11, as illustrated in the figures, so as to improve the stability of the implant 1 in the second bone 3 in three degrees of freedom. Of course, the deformable portion 5 may comprise two anchoring arms, or four anchoring arms, for example between two and eight anchoring arms, or more, without departing from the scope of the invention.

Preferably, the anchoring arms 9, 10, 11 are substantially parallel to each other, for example in a non-deformed configuration, such that their own axis of extension is parallel to the axis Y-Y', so as to be able to be deformed, for example, so as to converge towards one another, or at least their terminal ends 17 could converge.

Alternatively, the anchoring arms 9, 10, 11 may advantageously be convergent in a non-deformed configuration, for example slightly convergent, or on the contrary divergent. In the case where the anchoring arms 9, 10, 11 are convergent, the deformable portion 5 forms, for example, a beam of arms converging along the axis Y-Y'.

In the preferred case illustrated in the figures, the junction ends 16 of the three anchoring arms 9, 10, 11 are preferably arranged in Y (as illustrated in FIG. 4) or in T (as illustrated in FIG. 10) about the axis Y-Y', on the base end 7 of the anchoring body 4, such that the terminal ends 17 are also disposed respectively in Y or in T.

Preferably, in the case of the bent variant of the implant 1 represented in FIGS. 5 to 10, the junction ends 16 of the anchoring arms 9, 10, 11 are disposed in T.

For the case of the rectilinear variant of the implant 1 represented in FIGS. 1 to 4, the junction ends 16 of the anchoring arms are disposed in Y.

By <<disposed in T>>, is meant that two of the anchoring arms 10, 11 are disposed in opposition on either side of the axis Y-Y' so as to extend along a common midplane carried by said axis Y-Y', whereas the remaining anchoring arm 9 is disposed in a midplane orthogonal to said common midplane and carried by the axis Y-Y'. In this case, the axis Y-Y' forms the intersection of the common midplane and the orthogonal plane.

By <<disposed in Y>>, is meant that two of the anchoring arms 10, 11 are disposed on either side of the axis Y-Y' so as to extend along a common midplane parallel to the axis Y-Y' and spaced apart therefrom, whereas the remaining anchoring arm 9 is disposed in a midplane orthogonal to said common midplane and carried by the axis Y-Y'. In this case, the axis Y-Y' does not form the intersection of the common midplane and the orthogonal plane, the anchoring arms 9, 10, 11 are distributed around said axis Y-Y'.

In this configuration, two of the anchoring arms 10, 11 are preferably disposed symmetrically relative to a plane carried by the axis Y-Y', the third anchoring arm 9 being carried by this same plane of symmetry, and being the third anchoring arm 9 the shape of which is, in turn, symmetrical relative to said plane of symmetry. Preferably, the implant 1 substantially has a plane of symmetry carried by the axis Y-Y' and the axis of extension of the third anchoring arm 9. Two of the anchoring arms 10, 11 are preferably designed and shaped to be deformed in a privileged manner towards one another in a common plane, so as to form a clamp. In this preferred case, the last anchoring arm 9 is advantageously designed and shaped to be able to be deformed centripetally to the axis Y-Y'. Such a design allows improving the stability of the implant 1 within the second bone 3, and the reliability of its anchoring.

Preferably, at least one of the anchoring arms 9, 10, 11 has a section whose general shape is substantially trapezoidal. Thus, one of the anchoring arms 9, 10, 11, at least, preferably all the anchoring arms 9, 10, 11, has a prismatic general shape with a trapezoidal bottom, which allows promoting its flexibility according to predetermined directions, for example in the direction of the axis Y-Y'. Indeed, the distance between the opposite sides of the trapezoid forming the section of the anchoring arms 9, 10, 11 may be chosen so as to be smaller in the direction of deformation, and larger in the direction transverse to the deformation.

For example, the section of the anchoring arm 9 represented in the figures allows forming an anchoring arm 9 comprising:

an internal side 18 forming a face orientated in the direction of the axis Y-Y' and substantially ortho-radial thereto, an opposite external side 19, also substantially ortho-radial to the axis Y-Y', and two lateral sides 20 connecting the external side 19 to the internal side 18 and being, for example, radial to the axis Y-Y', or at least secant to the internal side 18 and to the external side 19.

Preferably, the internal side 18 is separated from the external side 19 by a radial distance $D_R$ smaller than an ortho-radial distance $D_O$ separating the lateral sides 20, so that the radial bending to the axis Y-Y' of the anchoring arm 9 is facilitated in comparison with an ortho-radial bending to the axis Y-Y'.

This particular shape results in that the anchoring arms 9, 10, 11 also have longitudinal ridges capable of blocking the implant 1 in rotation about the axis Y-Y' relative to the second bone 3.

The term <<substantially trapezoidal general shape>> advantageously comprises the case where certain sides of the trapezium are curved, in particular the internal side 18 and/or the external side 19. In particular, the external side 19 of the anchoring arms 9, 10, 11 may advantageously be curved. Preferably, the external side 19 of the general trapezoidal shape of the anchoring arm 9, 10, 11 advantageously forms an arc of a circle whose center is for example formed by the axis Y-Y', so that the external contour of the section orthogonal to the axis Y-Y' of the deformable portion 5 substantially forms a circle centered on said axis Y-Y' (as illustrated in FIGS. 4 and 10). In the non-deformed configuration, the anchoring arms 9, 10, 11 are preferably substantially parallel to each other and to the axis Y-Y', so that the deformable portion 5 has an external contour, which is for example formed by the union of the external sides 19 of the anchoring arms 9, 10, 11, having a substantially cylindrical or prismatic general shape about the axis Y-Y'.

Preferably, in a deformed configuration, the anchoring arms 9, 10, 11, which were initially parallel, converge, and for example their terminal ends 17 are brought to be tightened around the axis Y-Y', such that the external contour of the deformable portion 5 converges, and has for example a substantially truncated-cone general shape.

In turn, the internal side 18 may be preferably curved, so that the internal face of the anchoring arms 10, 11 forms a portion of a cylinder or concave cone of axis Y-Y', such that one portion of the free space E formed by the anchoring arms 10, 11 is substantially cylindrical or truncated-cone shaped, as can be seen in particular in FIG. 4 and FIG. 10.

The implant 1 preferably comprises a cannula 23 (FIGS. 1, 3, 4, 5 and 9) passing through the anchoring body 4 so as to prolong said free space E to the penetrating end 6. Thus, preferably, the cannula 23 is prolonged by the free space E delimited by the internal sides 18 of the anchoring arms 9, 10, 11, such that the implant 1 may be slidably threaded, via its cannula 23 and its free space E, onto a guiding rod, or a guiding pin, which facilitates the placement of the implant 1 in the patient's bones. The internal sides 18 of the anchoring arms 9, 10, 11 advantageously form a prolongation of the cannula 23 which has a substantially cylindrical shape with a diameter greater than the diameter of said cannula 23, so that the anchoring arms 9, 10, 11 have a clearance formed by the residual free space E formed between the guiding pin and the internal side 18, so as to be able to deform in the direction of the axis Y-Y' despite the presence of said guiding pin. Preferably, the implant 1 comprises a cannula 23 only if it forms a straight implant 1 such as illustrated for example in FIGS. 1 to 4, and not if it forms a bent implant as illustrated for example in FIGS. 5 to 10. Thus, the guiding rod, optionally rigid and rectilinear, may be inserted along the cannula 23, from the free space E, and the axes X-X' and Y-Y' which are coaxial and in alignment with one another.

Preferably, as illustrated in FIG. 4, the lateral sides 20 of two of the anchoring arms 10, 11 are parallel to each other and coplanar in pairs, such that the shape of the two concerned anchoring arms 10, 11 are delimited by two parallel planes common to said two anchoring arms 10, 11.

Moreover, as illustrated, for example, in FIGS. 5 to 10 (and in FIG. 2), at least one of the anchoring arms 9, 10, 11 is preferably provided with a longitudinal reinforcing fin 22 protruding beyond the anchoring arm 9, 10, 11 from a lateral side 20 of the latter, as this is particularly seen in FIG. 10. Preferably, the implant 1 comprises two longitudinal fins 22, carried respectively by two anchoring arms 10, whose lateral sides 20 are, for example, substantially coplanar, the longitudinal fins 22 rising parallel to one another in the direction of the axis Y-Y'. The longitudinal fins 22 advantageously allow both stiffening the concerned anchoring arm, but also, for example, contributing to allow rotational blocking about the axis Y-Y' of the implant 1 relative to the second bone 3 when it is anchored in the latter.

At least one of the anchoring arms 9, 10, 11, preferably two of the anchoring arms 10, 11, or even all of them, has a reduced section area 21 so as to promote the deformation of said anchoring arm 9, 10, 11 by bending of said anchoring arm at the reduced section area 21, towards or away from another one of the anchoring arms 9, 10, 11. As illustrated in FIGS. 5 to 10, the reduced section area 21 preferably forms a notch formed in the anchoring arm 9, 10, 11, in the vicinity of the junction end 16, the notch being advantageously open on the free space E and turned in the direction of another one of the anchoring arms 9, 10, 11 or the axis Y-Y', for example so that the concerned anchoring arm 9, 10, 11 could be bent at its reduced section 21 so as to converge towards another one of the anchoring arms 9, 10, 11. Each anchoring arm 9, 10, 11, preferably two of them, may thus be designed to be substantially rigid over most of its length, and to deform for example only at its reduced section 21 when it is biased by the second bone 3.

The anchoring body 4 extending along an axis X-X' from the base end 7 to the penetrating end 6, said anchoring body 4 comprising at least one longitudinal peripheral furrow 24 allowing rotatably blocking the implant 1 about the axis X-X' within the first bone 2, the longitudinal furrow 24 extending substantially parallel to the axis X-X' from the penetrating end 6 over at least one portion of the length of the anchoring body 4. The implant 1 advantageously comprises four peripheral longitudinal furrows 24, such that the anchoring body 4 has an orthogonal section that is substantially cruciform from the penetrating end 6 over at least one portion of its length. Preferably, the geometry of at least two peripheral furrows 24 is symmetrical relative to the axis X-X', as can be clearly seen in FIG. 3.

The longitudinal furrows 24 are advantageously disposed in the extension of the spaces formed between the anchoring arms 9, 10, 11, and in particular so as to prolong the extension planes associated with the lateral sides 20 of the anchoring arms 9, 10, 11. Alternatively, the longitudinal furrows 24 may on the contrary be arranged in the extension of the anchoring arms 9, 10, 11. The longitudinal furrows 24 may also be disposed so as not to be aligned with the anchoring arms 9, 10, 11, nor with the spaces formed between said anchoring arms 9, 10, 11.

The longitudinal furrows 24 are preferably separated by the longitudinal reinforcing ribs 12, which are for example aligned each with one of the anchoring arms 9, 10, 11, in order to extend in particular along a common axis of extension between the anchoring arm and the associated longitudinal reinforcing rib. The orthogonal section of the anchoring body 4 is thus advantageously in the form of a cross, each of the branches of which is formed by one of the longitudinal ribs 12.

The implant 1 may comprise more, or fewer longitudinal furrows 24 separated by the longitudinal ribs 12, for example depending on the considered number of anchoring arms 9, 10, 11, so that the anchoring body 4 has a star-shaped orthogonal section, each of the branches of which is formed by one of said longitudinal ribs 12.

Preferably, the longitudinal furrows 24 and the associated longitudinal ribs 12 extend over only a portion of the anchoring body 4 from the penetrating end 6, such that said longitudinal furrows 24 extend between said penetrating end 6 and a stop end 27 of said longitudinal furrows 24 located between said penetrating end 6 and the base end 7. According to this preferred configuration, the stop end 27 of the longitudinal furrows 24 allows stopping the implant 1 in translation along the axis X-X' during its anchoring in the first bone 2, when the latter comes into contact with said stop end 27.

The edge of the longitudinal furrows 24 preferably forms a protruding ridge, as illustrated in FIGS. 1 to 10, so as to improve the rotational blocking about the axis X-X' of the implant 1 in the first bone 2.

Moreover, the implant 1 is preferably provided with members for retaining said implant 1 in the bones.

At least one of the anchoring arms 9, 10, 11, preferably each of the anchoring arms 9, 10, 11, is advantageously provided with a primary member 28 for retaining said anchoring arm 9, 10, 11 in the second bone 3.

The primary retention member 28 is preferably formed by a line of primary retention teeth extending along the anchoring arm 9, 10, 11, and protruding centrifugally beyond the latter relative to the free space E.

As illustrated in FIGS. 1 to 10, the primary retention teeth are disposed on the external side 19 and rise radially relative to the axis Y-Y'. The primary retention member 28 is designed to oppose the removal of the implant 1 from the second bone 3, for example by hooking of said primary teeth on the internal wall of the medullary canal, while not substantially opposing the insertion of the implant 1 into said second bone 3. For this purpose, the primary teeth preferably have a gentle-sloped face, with a slight inclination relative to the axis Y-Y', directed towards the terminal end 17, and a steep-sloped face, with a high inclination relative to the axis Y-Y', for example orthogonal to the axis X-X' in the direction of the junction end 16.

The anchoring body 4 advantageously comprises at least one secondary member 29 for retaining the anchoring body 4 in the first bone 2, which is preferably formed by a line of secondary retention teeth extending along the anchoring body 4. As illustrated in FIGS. 1 to 10, the secondary retention teeth are disposed at the top of the longitudinal ribs 12 and rise radially relative to the axis X-X'. The secondary retention member 29 is designed to oppose the removal of the implant 1 from the first bone 2, for example by hooking of said secondary teeth on the internal wall of the medullary canal, while not substantially opposing the insertion of the implant 1 into said first bone 2. For this purpose, the secondary teeth preferably have a gentle-sloped face, with a slight inclination relative to the axis X-X', directed towards the penetrating end 6, and a steep-sloped face, with a high inclination relative to the axis X-X', for example orthogonal to the axis X-X' in the direction of the base end 7.

Thus, the anchoring of the implant 1 in the patient's bones is thus particularly reliable and durable, while being easy to carry out.

The invention also concerns, as such, an instrument for gripping 30 an implant 1 as previously described, the gripping instrument 30 comprising a removable bit 31 for securing the implant 1 with the gripping instrument 30, via the deformable portion 5 of said implant 1. An embodiment of a gripping instrument 30 in accordance with the invention is illustrated in FIGS. 11 to 14.

This gripping instrument 30 is advantageously designed to allow the gripping of a straight implant 1, as previously described.

The gripping instrument 30 preferably comprises a main body 32, for example with a generally elongated shape, extending along an axis Z-Z', and terminating in said securing bit 31. The latter advantageously allows removably grasping the implant 1 with the gripping instrument 30 via the deformable portion 5 of said implant 1. The securing bit 31 is preferably designed to receive the deformable portion 5 of said implant 1 so that the axis X-X' is coaxial with the axis Z-Z' when the implant 1 is secured to the gripping instrument 30. When the implant 1 is secured to the securing bit 31, the anchoring body 4 preferably protrudes beyond the latter so that the axis X-X' and the axis Z-Z' are coaxial.

The surgeon may thus advantageously grasp the implant 1 by means of the gripping instrument 30 in order to maneuver said implant 1 to anchor it to the first bone 2 and/or the second bone 3.

The securing bit 31 preferably has a generally cylindrical external shape about the axis Z-Z'. As illustrated in FIG. 12, it preferably comprises an orifice 34 for receiving the deformable portion 5 of the implant 1, said receiving orifice preferably being cruciform or, for example, star shaped, in order to rotatably block the implant 1 about the axis Z-Z' relative to the gripping tool 30. The cruciform or star shape advantageously corresponds to the external contour of the deformable portion 5 of the implant 1, and in particular to the arrangement of the anchoring arms 9, 10, 11, which may be inserted into the four notches or branches of the cruciform shape in order to be able to be driven in rotation about the axis Z-Z' by the surgeon, by means of the gripping instrument 30.

The gripping instrument 30 preferably comprises a removable handle 33 removably and integrally connected to the main body 32. The removable handle 33 may advantageously constitute a privileged gripping area of the gripping instrument 30 by the surgeon. Alternatively, the main body 32 may be connected to a machine in order to maneuver the implant via said machine.

Finally, the invention concerns, as such, an instrument for gripping 30 an implant 1 as described hereinbefore, and in particular the anchoring body 4 of which extends along an axis X-X', the deformable portion 5 extending in a direction opposite to the anchoring body 4 along an axis Y-Y' secant to the axis X-X', so that the axis Y-Y' is inclined relative to the axis X-X' at an elevation angle α comprised between:

8 and 12 degrees, preferably about 10 degrees, or
15 and 19 degrees, preferably about 17 degrees.

Thus, this gripping instrument 30 may advantageously be used to perform the gripping of a bent implant 1, as previously described.

The gripping instrument 30 of the invention comprises a main body 32 extending along an axis Z-Z' and terminating in a removable bit 31 for securing the implant 1 with the gripping instrument 30, via the deformable portion 5 of said implant 1, the securing bit 31 being designed to receive the deformable portion 5 of said implant 1 so that the axis Y-Y' is secant to the axis Z-Z' at a compensation angle β equal to the elevation angle α, so as to compensate for the inclination of the axis Y-Y' relative to the axis X-X', such that the axis X-X' is coaxial with the axis Z-Z' when the implant 1 is secured to the gripping instrument 30.

The securing bit 31 preferably has a generally cylindrical outer shape about the axis Z-Z'. As illustrated in FIG. 12, it preferably comprises a receiving orifice 34 of the deformable portion 5 of the implant 1, said receiving orifice being preferably cruciform or, for example, star shaped, in order to rotatably block the implant 1 about the axis Y-Y' and/or X-X' and/or Z-Z' relative to the gripping tool 30. The cruciform or star shape advantageously corresponds to the external contour of The deformable portion 5 of the implant 1, and in particular to the arrangement of the anchoring arms 9, 10, 11, which may be inserted into the four notches or branches of the cruciform shape in order to be able to be driven in rotation about the axis Y-Y' and/or X-X' and/or Z-Z' by the surgeon, by means of the gripping instrument 30.

The features of the gripping instrument 30 for a straight implant 1, whose axis X-X' and axis Y-Y' are coaxial, preferably shall also apply mutatis mutandis to this gripping instrument 30 for a bent implant 1.

Finally, an example of a surgical method for implanting the implant 1 previously described in the body of a patient or an animal will be described hereinafter.

The method includes in particular the following steps, carried out preferably in the following order:

An incision is performed in the body of a patient in order to reach the first bone 2 and the second bone 3.

The articulation connecting the first bone 2 to the second bone 3 is sectioned in order to uncover the external portions of said first bone 2 and second bone 3.

The end of said first bone 2 and second bone 3 is removed, for example by piercing it, in order to clear the medullary canals of said first bone 2 and second bone 3, for example, using an opening instrument 26 shown in FIGS. 15 and 16.

The interior of the medullary canals is partially or totally hollowed in order to prepare a free space to allow the insertion of the deformable portion 5 and the anchoring body 4 of the implant 1 respectively into each of said medullary canals.

The implant 1 is grasped using the gripping instrument 30, as illustrated for example in FIG. 13, such that the anchoring body 4 protrudes from the securing bit 31, and that the axes X-X' and Z-Z' are coaxial.

The implant 1 is anchored, optionally forcibly, in the medullary canal of the first bone 2 (as illustrated in FIG. 14), via the anchoring body 4.

The gripping instrument 30 is disengaged from the implant 1.

The second bone 3 is threaded onto the deformable portion 5 of the implant 1.

The method may also include a step of adding an osteoinductive material into the medullary canals, or around the implant 1 when it is anchored. Certain steps of the method described hereinbefore might advantageously be omitted, or carried out in a different order.

POSSIBILITY OF INDUSTRIAL APPLICATION

The invention finds its industrial application in the design, the realization and the implementation of arthrodesis implants allowing promoting the bone fusion of a first bone with a second bone, as well as instruments for gripping such implants.

The invention claimed is:

1. An interphalangeal arthrodesis implant (1) allowing promoting the bone fusion of a first bone (2) with a second bone (3), said implant (1) comprising:
a substantially rigid and non-deformable, elongated anchoring body (4), designed to ensure the anchoring of the implant (1) in the first bone (2), the anchoring body (4) extending along an axis (X-X') between an end (6) for penetration in said first bone (2) and an opposite base end (7), the end (6) for penetration forming a free end of the implant (1) and the opposite base end (7) forming an attachment point of the implant (1), said anchoring body (4) including at least one peripheral longitudinal furrow (24) extending substantially parallel to the axis (X-X') from the end (6) for penetration over at least a portion of a length of the anchoring body (4), to substantially block rotation of the anchoring body (4) about the axis (X-X') of the implant (1) within the first bone (2), and
a deformable portion (5) designed to ensure the anchoring of the implant (1) in the second bone (3), said deformable portion (5) extending in a direction opposite to the anchoring body (4) along an axis (Y-Y') and comprising at least two discrete anchoring arms (9, 10, 11) which protrude beyond the anchoring body (4) from the attachment point of the implant (1) at the base end (7) of the anchoring body (4), the anchoring arms (9, 10, 11) being separated from each other by a free space (E) so as to be able to be brought closer to each other by deformation of said anchoring arms under the action of the second bone (3),
wherein at least one of the anchoring arms (9, 10, 11) is provided with a primary retention member (28) for retaining said anchoring arms (9, 10, 11) in the second bone (3), wherein the primary retention member (28) is formed by a line of primary retention teeth extending along the anchoring arms (9, 10, 11), and protruding centrifugally beyond the anchoring arms (9, 10, 11) relative to the free space (E),
wherein at least one of the anchoring arms (9, 10, 11) is provided with a longitudinal reinforcing fin (22) protruding beyond the anchoring arm (9, 10, 11) from a lateral side (20) of the anchoring arm (9, 10, 11), to allow both stiffening of the anchoring arm (9, 10, 11) and blocking rotation about the axis (Y-Y') of the implant (1) relative to the second bone (3) when the implant (1) is anchored in the second bone (3),
wherein the anchoring arms (9, 10, 11) are substantially parallel to each other,
wherein the first bone (2) in which the anchoring body (4) is adapted to be anchored is a first phalange, and the second bone (3) in which the deformable portion (5) is adapted to be anchored is a second phalange of the same finger as the first phalange, the anchoring body (4) being adapted to be anchored in a medullary canal of the first bone (2), the deformable portion (5) being adapted to be anchored in a medullary canal of the second bone (3).

2. The implant (1) according to claim 1, wherein the deformable portion (5) is formed by three anchoring arms (9, 10, 11).

3. The implant (1) according to claim 1, wherein the deformable portion (5) has an external contour with a substantially cylindrical or prismatic general shape.

4. The implant (1) according to claim 1, wherein at least one of the anchoring arms (9, 10, 11) has a reduced section area (21) so as to promote the deformation of said anchoring arms (9, 10, 11) by bending of said anchoring arms at the reduced section area (21), toward or away from another of the anchoring arms (9, 10, 11).

5. The implant (1) according to claim 1, wherein at least one of the anchoring arms (9, 10, 11) has a section whose general shape is substantially trapezoidal, an external side (19) of the general trapezoidal shape forming an arc of a circle so that the external contour of an orthogonal section of the deformable portion (5) substantially forms a circle.

6. The implant (1) according to claim 1, wherein the deformable portion (5) extends in the opposite direction of the anchoring body (4) along the axis (Y-Y') which is coaxial with the axis (X-X').

7. The implant (1) according to claim 1, wherein each of the anchoring arms (9, 10, 11) extends between a junction end (16) of the anchoring arms (9, 10, 11) interfacing with the anchoring body (4) and an opposite terminal end (17) of the anchoring arm (9, 10, 11) for implanting said anchoring arm (9) in the second bone (3), two of the anchoring arms (10, 11) being disposed on either side of the axis (Y-Y') extending in the direction of extension of the deformable portion, so as to extend along a common midplane parallel to the axis (Y-Y') and spaced from the axis (Y-Y').

8. The implant (1) according to claim 1, wherein the deformable portion (5) extends in a direction opposite to the anchoring body (4) along the axis (Y-Y') which is secant to the axis (X-X'), such that the axis (Y-Y') is inclined relative to the axis (X-X') at an elevation angle (a) comprised between:
a) 8 and 22 degrees, or
b) 15 and 19 degrees.

9. The implant (1) according to claim 8, wherein the anchoring body (4) has an external surface (8) connecting the base end (7) to the end (6) for penetration, the external surface (8) being generally convergent in shape along the axis (X-X'), in a direction towards the end (6) for penetration.

10. The implant (1) according to claim 1, wherein the anchoring body (4) of the implant is cannulated.

11. The implant (1) according to claim 1, wherein the implant comprises four peripheral longitudinal furrows (24), such that the anchoring body (4) has a substantially cruciform orthogonal section from the end (6) for penetration over at least one portion of its length.

12. The implant (1) according to claim 1, wherein the anchoring body (4) comprises at least one secondary member (29) for retaining the anchoring body (4) in the first bone (2).

13. The implant (1) according to claim 1, wherein the implant forms a one-piece single part, the deformable portion (5) being integral with the anchoring body (4).

14. The implant (1) according to claim 1, wherein the implant is made of a PEEK polymer material.

15. The implant according to claim 1, wherein the anchoring body comprises at least one secondary member for retaining the anchoring body in the first bone, said at least one secondary member including a line of secondary retention teeth extending along the anchoring body.

16. The implant according to claim 1, wherein at least two of the anchoring arms have respective co-planar lateral sides, and each of the co-planar lateral sides of the respective anchoring arms includes one or more longitudinal reinforcing fins protruding therefrom and configured to block rotation of the implant about the axis (Y-Y').

17. An interphalangeal arthrodesis implant (1) allowing promoting the bone fusion of a first bone (2) with a second bone (3), said implant (1) comprising:
a substantially rigid and non-deformable, elongated anchoring body (4), designed to ensure the anchoring of the implant (1) in the first bone (2), the anchoring body (4) extending between an end (6) for penetration in said first bone (2) and an opposite base end (7), and
a deformable portion (5) designed to ensure the anchoring of the implant (1) in the second bone (3), said deformable portion (5) extending in a direction opposite to the anchoring body (4) along an axis (Y-Y') and comprising at least two discrete anchoring arms (9, 10, 11) which protrude beyond the anchoring body (4) from the base end (7) of the anchoring body (4), the anchoring arms (9, 10, 11) being separated from each other by a free space (E) so as to be able to be brought closer to each other by deformation of said anchoring arms under the action of the second bone (3),
wherein at least one of the anchoring arms (9, 10, 11) is provided with a primary retention member (28) for retaining said anchoring arms (9, 10, 11) in the second bone (3), wherein the primary retention member (28) is formed by a line of primary retention teeth extending along the anchoring arms (9, 10, 11), and protruding centrifugally beyond the anchoring arms (9, 10, 11) relative to the free space (E),
wherein at least one of the anchoring arms (9, 10, 11) is provided with a longitudinal reinforcing fin (22) protruding beyond the anchoring arm (9, 10, 11) from a lateral side (20) of the anchoring arm (9, 10, 11), to allow both stiffening of the anchoring arm (9, 10, 11) and blocking rotation about the axis (Y-Y') of the implant (1) relative to the second bone (3) when the implant (1) is anchored in the second bone (3), and
wherein at least one of the anchoring arms (9, 10, 11) has a section being generally trapezoidal in shape, said section forming the anchoring arm (9, 10, 11) comprising:
an internal side (18) forming a face orientated in the direction of the axis (Y-Y') and substantially ortho-radial thereto,
an opposite external side (19) substantially ortho-radial to the axis (Y-Y'), and
two lateral sides (20) connecting the external side (19) to the internal side (18) and being secant to the internal side (18) and to the external side (19),
wherein said internal side (18) is separated from the external side (19) by a radial distance ($D_R$) smaller than an ortho-radial distance ($D_O$) separating the lateral sides (20),
wherein the anchoring arms (9, 10, 11) are substantially parallel to each other,
wherein the first bone (2) in which the anchoring body (4) is adapted to be anchored is a first phalange, and the second bone (3) in which the deformable portion (5) is adapted to be anchored is a second phalange of the same finger as the first phalange, the anchoring body (4) being adapted to be anchored in a medullary canal of the first bone (2), the deformable portion (5) being adapted to be anchored in a medullary canal of the second bone (3).

* * * * *